(12) United States Patent
Schaller et al.

(10) Patent No.: US 11,759,237 B2
(45) Date of Patent: Sep. 19, 2023

(54) RETRACTABLE CANNULA ASSEMBLY

(71) Applicant: Alcon Inc., Fribourg (CH)

(72) Inventors: Philipp Schaller, Stein am Rhein (CH); Reto Grueebler, Greifensee (CH); Thomas Linsi, Schaffhausen (CH)

(73) Assignee: Alcon Inc., Fribourg (CH)

( * ) Notice: Subject to any disclaimer, the term of this patent is extended or adjusted under 35 U.S.C. 154(b) by 408 days.

(21) Appl. No.: 16/903,865

(22) Filed: Jun. 17, 2020

(65) Prior Publication Data
US 2020/0397477 A1    Dec. 24, 2020

Related U.S. Application Data

(60) Provisional application No. 62/865,344, filed on Jun. 24, 2019.

(51) Int. Cl.
| | | |
|---|---|---|
| *A61B 17/34* | (2006.01) | |
| *A61F 9/007* | (2006.01) | |
| *A61B 17/00* | (2006.01) | |

(52) U.S. Cl.
CPC ...... *A61B 17/3496* (2013.01); *A61B 17/3421* (2013.01); *A61B 17/3498* (2013.01); *A61F 9/007* (2013.01); *A61B 2017/00199* (2013.01); *A61B 2017/00477* (2013.01); *A61B 2017/3454* (2013.01); *A61B 2217/005* (2013.01); *A61B 2217/007* (2013.01)

(58) Field of Classification Search
CPC ............ A61B 17/3496; A61B 17/3421; A61B 2017/00199; A61B 2017/00477; A61B 2017/3454; A61F 9/007
See application file for complete search history.

(56) References Cited

U.S. PATENT DOCUMENTS

| | | | |
|---|---|---|---|
| 5,391,153 A | * | 2/1995 | Haber ................ A61B 17/3462 604/167.01 |
| 5,549,627 A | * | 8/1996 | Kieturakis ............. A61B 17/29 606/206 |
| 9,192,515 B2 | | 11/2015 | Papac |
| 9,730,834 B2 | | 8/2017 | Charles |
| 9,731,065 B2 | | 8/2017 | Bourne |
| 9,750,637 B2 | | 9/2017 | Schaller |

(Continued)

FOREIGN PATENT DOCUMENTS

CN    202426711 U    9/2012

OTHER PUBLICATIONS

DORC: Focus on Highlights catalog, 2012, pp. 9-11, 20, 34, 35.

(Continued)

*Primary Examiner* — Sarah A Long
(74) *Attorney, Agent, or Firm* — PATTERSON + SHERIDAN, LLP

(57) ABSTRACT

Disclosed herein are surgical instruments used in ophthalmic surgical procedures and associated methods. Particular embodiments relate to a cannula assembly having a cannula tip that is retractable. The cannula assembly may comprise a cannula hub. The cannula assembly may further comprise an outer tube that extends from a distal end the cannula hub. The cannula assembly may further comprise an inner tube that extends from the distal end of the cannula hub and is disposed in the outer tube, wherein the inner tube has a cannula tip that extends from the outer tube and is retractable into the outer tube.

20 Claims, 6 Drawing Sheets

(56) References Cited

U.S. PATENT DOCUMENTS

| | | | |
|---|---|---|---|
| 9,757,536 B2 | 9/2017 | Abt | |
| 9,878,075 B2 | 1/2018 | Sussman | |
| 2002/0156465 A1* | 10/2002 | Overaker | A61B 17/2909 606/1 |
| 2002/0161398 A1* | 10/2002 | Hickingbotham | A61B 17/2909 606/206 |
| 2007/0260173 A1 | 11/2007 | Boukhny | |
| 2008/0167604 A1 | 7/2008 | Hong | |
| 2014/0018732 A1* | 1/2014 | Bagaoisan | A61M 25/0136 604/95.04 |
| 2016/0067091 A1 | 3/2016 | Wells | |
| 2018/0296391 A1 | 10/2018 | Charles | |
| 2019/0374248 A1 | 12/2019 | Grueebler | |
| 2020/0178993 A1* | 6/2020 | Ebrahimi | A61B 34/20 |
| 2020/0188561 A1 | 6/2020 | Grueebler | |
| 2020/0397476 A1 | 12/2020 | Schaller | |

OTHER PUBLICATIONS

Alcon Global Vitreoretinal Product Catalog, 2014 (pp. 41-48).
https://www.vitreq.com/uploads/brochures/Vitreq_BVI_Brochure_Backflush_2018.pdf (accessed May 29, 2020, appears to be dated Jun. 2018 (8 pages).
MedOne Backflush Cannulas brochure, dated 2018 (1 page).
MedOne Brochure, "Exactly What Your Looking For—High Quality Instruments for Vitreoretinal Surgery," 2012, 12pages.

* cited by examiner

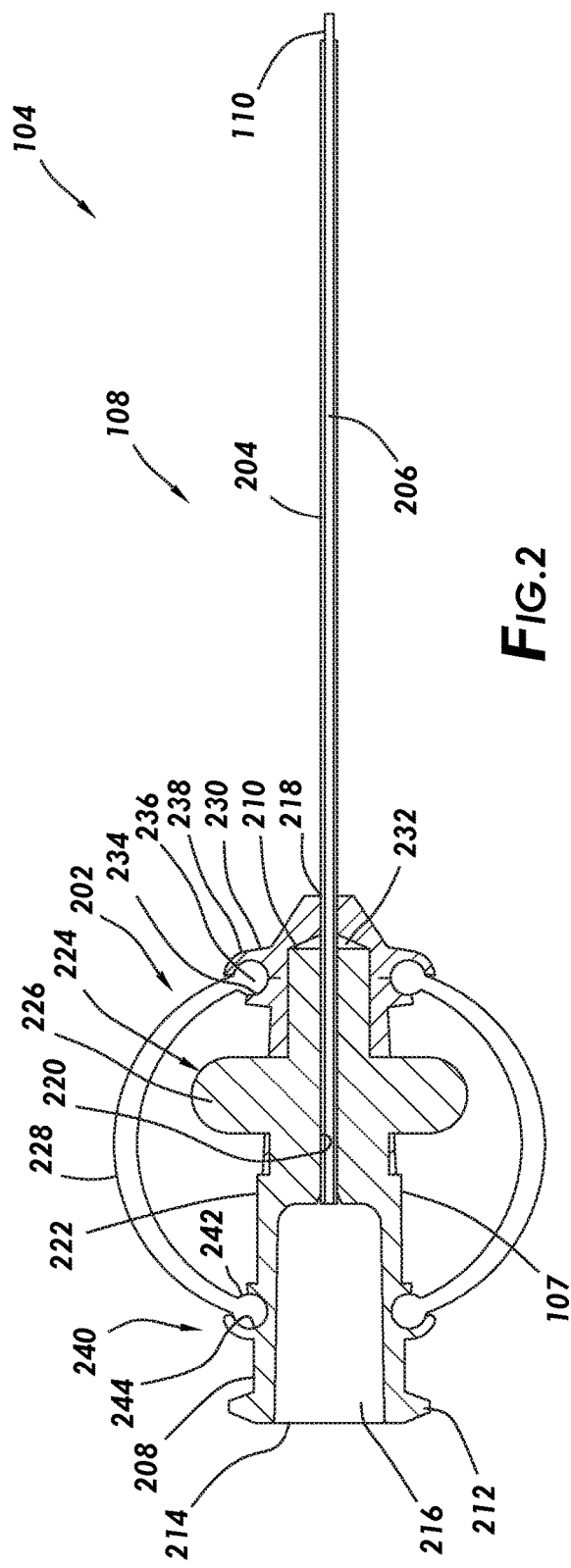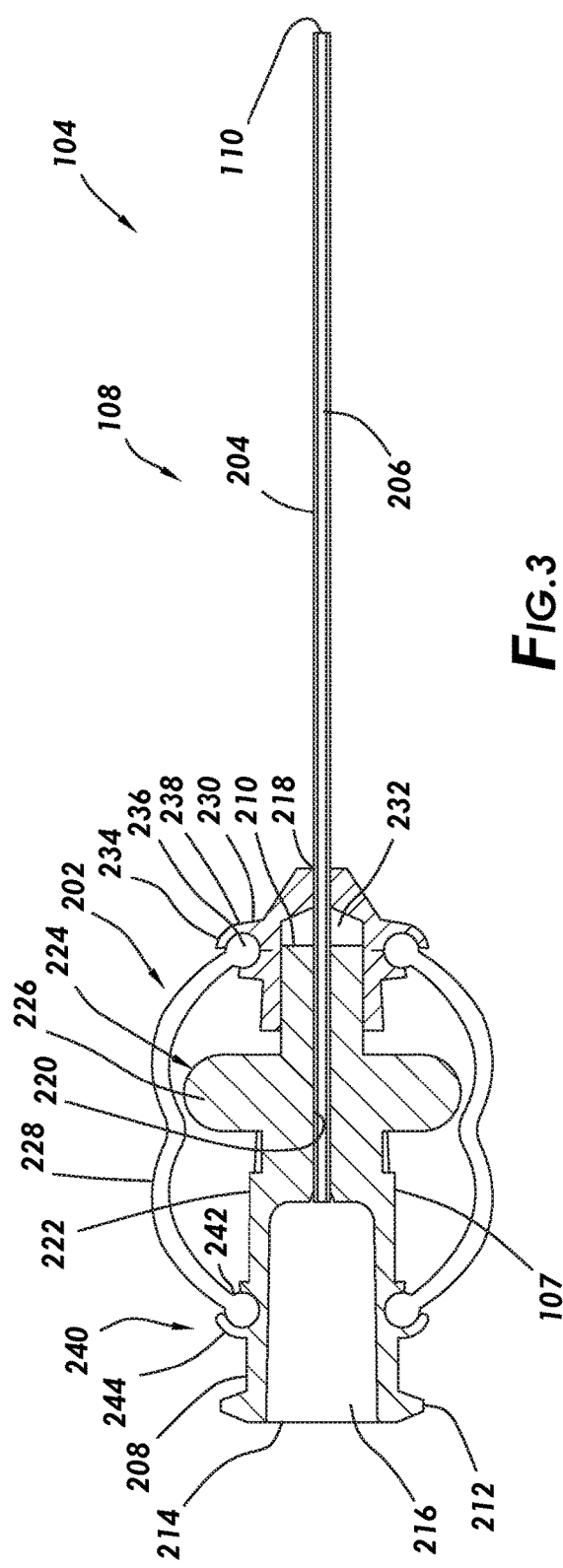

RETRACTABLE CANNULA ASSEMBLY

PRIORITY CLAIM

This application claims the benefit of priority of U.S. Provisional Patent Application Ser. No. 62/865,344 titled "Retractable Cannula Assembly", filed on Jun. 24, 2019, whose inventors are Philipp Schaller, Reto Grueebler, and Thomas Linsi, which is hereby incorporated by reference in its entirety as though fully and completely set forth herein.

TECHNICAL FIELD

The present disclosure generally relates to surgical instruments used in ophthalmic surgical procedures and, more particularly, to a cannula assembly having a cannula tip that is retractable.

BACKGROUND

Cannulas are one example of microsurgical instruments used in ophthalmic surgical procedures, such as retinal detachment surgery. By way of example, cannulas may be used to aspirate fluids such as blood, aqueous humor, and/or infusion fluids (e.g., balanced saline solutions). These cannulas are typically connected by tubing to a machine-induced vacuum source and the fluids are collected in a disposable cassette (e.g., at a control console). To prevent or avoid damage to the eye tissue in the event of contact with the eye, the cannula may have a tip formed from a soft, compliant material (e.g., silicone). This "soft" tip should help prevent damage to the delicate tissue of the eye in the event of physical contact with the eye, typically the retina.

During ophthalmic surgical procedures, the surgeon may require several different instruments throughout the procedure. This frequently requires that these instruments be repeatedly and/or sequentially inserted into and removed out of an incision that provide access to an interior portion of the eye. To guard against trauma to the incision from the repeated entry/exit of instruments, surgeons generally insert the instruments through an access cannula. One type of access cannula includes a narrow tube with an attached hub. The surgeon may make an incision on the eye (e.g., with a trocar through the sclera) and insert the tube of the access cannula through the incision up to the hub, which acts as a stop that prevents the tube from entering the eye completely. Valved cannulas were developed to address the issue of fluids flowing out of the tube when the tube is not connected to an infusion device, or when an instrument is not inserted within the tube, because the interior of the eye is pressurized. In some instances, valved cannulas include a slit silicone diaphragm or cap on the outside of the hub. The slit provides an opening into the tube through which the surgical instrument can be inserted. However, a soft-tipped cannula may be insufficiently rigid to effectively open the slit without the application of undue pressure against the cannula. The soft tip may buckle or become stuck necessitating multiple trials before successful entry through the access cannula into the eye. If too much pressure applied, the soft tip could even be sheared off, potentially falling into the eye during insertion and requiring remedial measures for removal of the soft tip from the eye.

SUMMARY

In an exemplary embodiment, the present disclosure provides an apparatus for use in an ophthalmic surgical procedure. The apparatus may include a cannula assembly that includes a cannula hub. The cannula assembly may further include an outer tube that extends from a distal end the cannula hub. The cannula assembly may further include an inner tube that extends from the distal end of the cannula hub and is disposed in the outer tube, wherein the inner tube has a cannula tip that extends from the outer tube and is retractable into the outer tube.

In another exemplary embodiment, the present disclosure provides a system for ophthalmic surgical procedures. The system may include a console including a housing, a display screen supported by the console, and a processor. The system may include a cannula assembly that includes a cannula hub. The system may further include an outer tube that extends from a distal end the cannula hub. The system may further include an inner tube that extends from the distal end of the cannula hub and is disposed in the outer tube, wherein the inner tube has a cannula tip that extends from the outer tube and is retractable into the outer tube. The system may further include a supply line configured to couple the cannula assembly to the console.

In yet another exemplary embodiment, the present disclosure provides a method for operating a surgical instrument. The method may include providing a cannula assembly. The cannula assembly may include a cannula hub, an outer tube that extends from a distal end of the cannula hub, and an inner tube that extends from the distal end cannula hub and is disposed in the outer tube. The inner tube may have a cannula tip that extends from the outer tube. The method may further include retracting the cannula tip of the inner tube into the outer tube. The method may further include inserting the cannula assembly through a working cannula and into an eye while the cannula tip is retracted into the outer tube.

It is to be understood that both the foregoing general description and the following drawings and detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following.

BRIEF DESCRIPTION OF THE DRAWINGS

These drawings illustrate examples of certain aspects of some of the embodiments of the present disclosure and should not be used to limit or define the disclosure.

FIG. 2 is a cross-sectional side view of an example surgical instrument with a cannula tip in an extended position according to particular embodiments of the present disclosure.

FIG. 3 is a cross-sectional side view of the example surgical instrument of FIG. 2 in a retracted position according to particular embodiments of the present disclosure.

DETAILED DESCRIPTION

Figure 1:
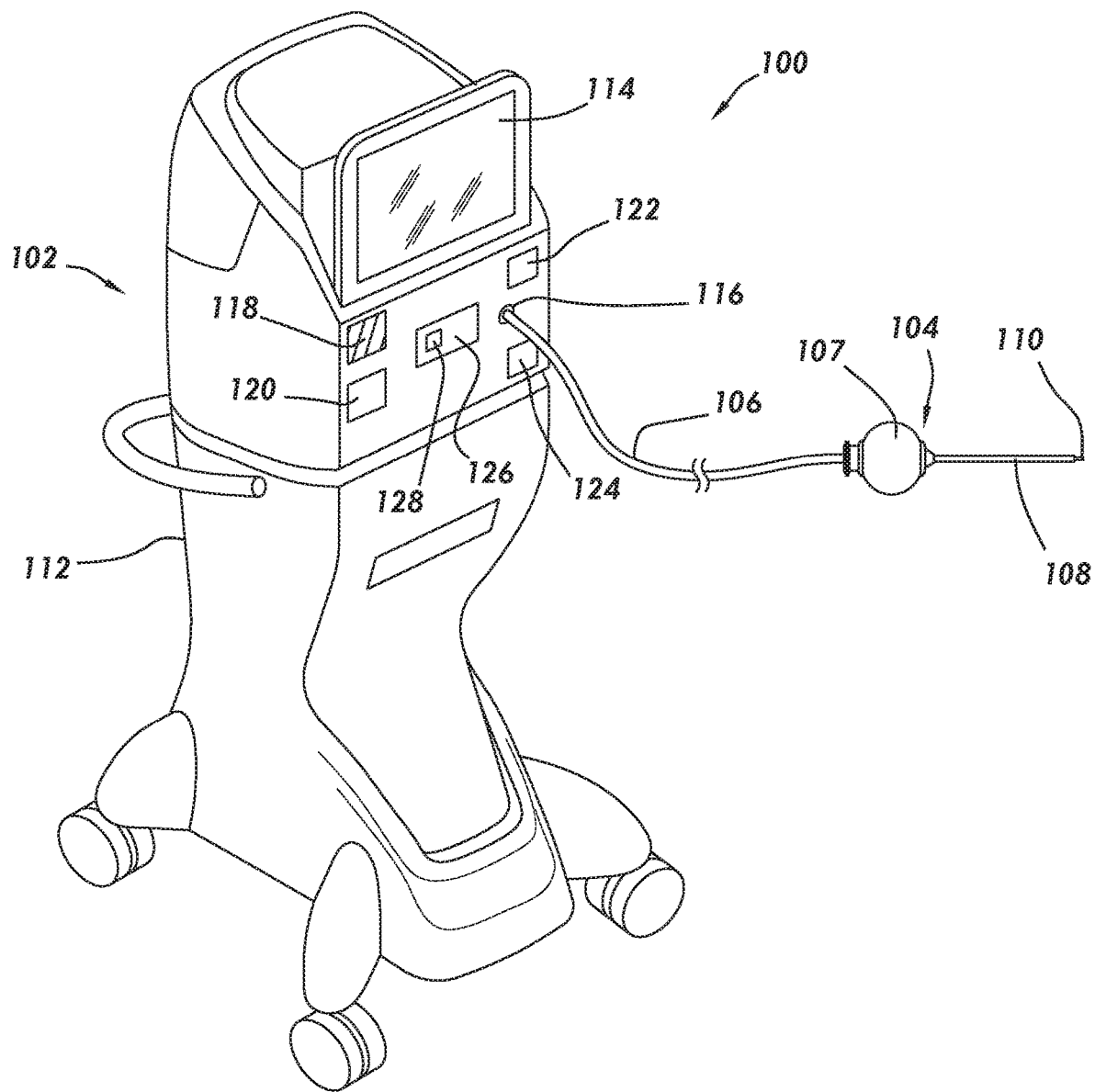
FIG. 1 illustrates an example surgical system according to particular embodiments of the present disclosure.

For the purposes of promoting an understanding of the principles of the present disclosure, reference will now be made to the implementations illustrated in the drawings and specific language will be used to describe them. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with reference to one or more implementations may be combined with the features, components, and/or steps described with reference to other implementations of the present disclosure. For simplicity, in some instances the same reference numbers are used throughout the drawings to refer to the same or like parts.

The present disclosure generally relates to surgical instruments used in ophthalmic surgical procedures and, more particularly, embodiments relate to a cannula assembly having a cannula tip that is retractable. Certain cannula tips, such as soft tips, may be difficult to insert into the eye through the working cannula. In accordance with example embodiments disclosed herein, the cannula assembly may be provided with a cannula tip that is retractable. During insertion in the eye, the cannula tip may be retracted, for example, to facilitate insertion through the working cannula. After insertion into the eye, the cannula tip may be extended prior to use. Therefore, the apparatus, systems, and methods of the present embodiments may allow for insertion of the soft-tipped cannula assemblies through the working cannula and into the eye without buckling or potential damage to the soft tip.

FIG. 1 illustrates a surgical system 100 according to particular example embodiments. As illustrated, the surgical system 100 may include a console 102, a surgical instrument 104, and a supply line 106 coupling the surgical instrument 104 to the console 102. In the illustrated embodiment, the surgical instrument 104 includes a cannula hub 107 and a cannula assembly 108 having a cannula tip 110 that is retractable. Cannula assembly 108 may be attached to the cannula hub 107. One embodiment of the surgical instrument 104 will be described in more detail below with respect to FIG. 2. It should be understood that the surgical system 100 shown in FIG. 1 is merely an example, and the surgical instrument 104 may be used with systems with alternative configurations.

In some embodiments, the console 102 may include a housing 112 and an associated display screen 114. As illustrated, the housing 112 may be mobile base that supports the display screen 114 and other components of the console 102. The display screen 114 may show data relating to system operation and performance during a surgical procedure. During ophthalmic surgery, the surgical instrument 104 may be coupled to the console 102 by the supply line 106. By way of example, the supply line 106 may include flexible plastic, silicone, or rubber tubing and/or electric cabling. In some embodiments, the supply line 106 may be fluidically coupled with a surgical cassette (not shown) to operatively connect to the surgical instrument 104 through one or more ports 116 in the housing 112. In some embodiments, the supply line 106 includes aspiration lines, power lines, and/or irrigation lines. In some embodiments, the supply line 106 may facilitate control and monitoring to the surgical instrument 104 by also transmitting data between the surgical instrument 104 and the console 102. In other embodiments, data may be transferred wirelessly between the surgical instrument 104 and the console 102.

In some embodiments, the console 102 further may include one or more processors 118 in communication with a memory 120. The processor 118 may include computer-instructions to control the surgical instrument 104, display information on the display screen 114, and/or receive and process input commands and data. In some embodiments, the surgical system 100 may include a data transmission module 122. In some embodiments, the surgical system 100 may include a network interface 124 for communication with a network. In the illustrated embodiment, the surgical system 100 includes a user interface 126 that enables the user to input data and/or command signals.

For example, in one embodiment, the user interface 126 may include a control element 128 that allows the user to trigger a state change in the surgical instrument 104. In some embodiments, the control element 128 includes a button that may be depressed to activate the state change. In other embodiments, the control element 128 includes a plurality of buttons with each button configured to activate and/or deactivate different functions of the surgical instrument 104. However, the control element 128 may include any of a variety of ON/OFF switches, buttons, toggles, wheels, or other user input devices. In some embodiments, the control element 128 may be additionally or alternatively disposed on the surgical instrument 104. These features may facilitate control of the surgical instrument 104 during operation.

The processor 118 may be any suitable processor, including, but not limited to, an integrated circuit with power, input, and output pins capable of performing logic functions. For example, the processor 118 may perform logic functions based on inputs from the control element 128 to affect the state change of the surgical instrument 104. In some embodiments, the processor 118 controls the supply of power from a power source (not shown) to the surgical instrument 104 and/or signal commands to the surgical instrument 104. In various embodiments, the processor 118 may be a targeted device controller or a microprocessor configured to control more than one component of the surgical instrument 104 or a combination thereof. The processor 118 may include one or more programmable processor units running programmable code instructions for controlling the surgical instrument 104, among other functions. For example, in some embodiments, the processor 118 can control the aspiration and/or backflush functions of the surgical instrument 104.

The processor 118 may be wirelessly coupled to a computer (not shown) and/or other types of processor-based devices suitable for a variety of ocular applications. In various embodiments, the processor 118 can receive input data from a user, the control element 128, the surgical instrument 104, and/or various accessory devices via wireless or wired mechanisms. The processor 118 may use such input data to generate control signals to control or direct the operation of the surgical instrument 104. In some embodiments, the processor 118 is in direct wireless communication with the surgical instrument 104 and can receive data from and send commands to the surgical instrument 104.

The memory 120 may any suitable memory, including, but not limited to, semiconductor memory, such as Random-Access Memory (RAM), Ferroelectric RAM (FRAM), or flash memory, for interfacing with the processor 118. As such, the processor 118 can write to and read from the memory 120, and perform other common functions associated with managing semiconductor memory. For example, a series of tissue characterizations and/or command sequences can be stored in the memory 120.

FIGS. 2 and 3 illustrate a cross-sectional side view of the cannula assembly 108 according to embodiments of the present disclosure. FIG. 2 illustrates the cannula tip 110 in an initial (or extended) position. FIG. 3 illustrates the cannula assembly 108 in a retracted position with the cannula tip 110 being fully retracted. As illustrated, the cannula assembly 108 may include a cannula hub 107, an actuator 202, an outer tube 204, and an inner tube 206. The actuator 202 may be operable to retract the cannula tip 110 from an initial position (FIG. 2) to a retracted position (FIG. 3). It should be understood that the term "retracted" is intended to cover both withdrawal of the cannula tip 110 into the outer tube 204 in addition to extension of the outer tube 204 to cover the cannula tip 110. The term "retracted" is broadly intended to imply that the cannula tip 110 is positioned in the outer tube 204. The cannula assembly 108 may be used with any suitable instrument. In some embodiments, the cannula assembly 108 may be attached to the cannula hub 107 (e.g., shown on FIG. 1), which may be syringe, aspiration handle, or other suitable instrument. In other embodiments, the cannula assembly 108 may be attached directly to tubing (e.g., supply line 106 on FIG. 1).

The cannula hub 107 may include a proximal end 208 and a distal end 210. In the illustrated embodiment, the proximal end 208 includes a rim 212 and a proximal opening 214. The cannula hub 107 may define an inner chamber 216 opening into the proximal opening 214. While not shown, embodiments of the inner chamber 216 may receive a distal end of an instrument (e.g., cannula hub 107 on FIG. 1) or tubing (e.g., supply line 106 on FIG. 1) for mounting the cannula hub 107. The distal end 210 of the cannula hub 107 may include a distal opening 218. In the illustrated embodiment, the cannula hub 107 may further define a lumen 220 that extends from the inner chamber 216 to the distal opening 218. In some embodiments, the lumen 220 may receive at least a portion of the cannula assembly 108. For example, the lumen 220 may receive the outer tube 204 and/or the inner tube 206. The cannula hub 107 may include an outer surface 222 extending between the proximal end 208 and the distal end 210. The cannula hub 107 may also include one or more stops 224. The stops 224 may be any suitable device for limiting movement of the actuator 202. For example, the stops 224 may include one or more protuberances 226 that extend from the outer surface 222 of the cannula hub 107. In the illustrated embodiment, the stops 224 may include a pair of opposing stops 224.

The actuator 202 may be any suitable device for retracting the cannula tip 110 into the outer tube 204. For example, the actuator 202 may include a flexural element 228. The flexural element 228 may be from a material that is flexible and elastic so that the flexural element 228 may flex when force is applied but return to its original position when the force is removed. Suitable flexible materials may include, but are not limited to, plastics and metals. An example of a specific flexible material may include a polycarbonate. When flexed or otherwise deformed, the flexural element 228 may store spring energy in the form of a biasing force to return to its original position when the force is removed. By pressing flexural element 228 in the radial direction, in some embodiments, the flexural element 228 may deform and move the outer tube 204 distally with respect to the cannula hub 107. For example, the flexural element 228 may deform and extend longitudinally to move the outer tube 204. In the illustrated embodiment, the flexural element 228 is arcuate in shape and is coupled at one end to the cannula hub 107 and at the other end to the outer tube 204.

In some embodiments, a connector piece 230 interconnects the flexural element 228 and the outer tube 204. The connector piece 230 may be any suitable device for coupling the flexural element 228 and the outer tube 204 such that the outer tube 204 moves with deformation of the flexural element 228. As illustrated, the connector piece 230 may include a proximal chamber 232 that receives the distal end 210 of the cannula hub 107. The connector piece 230 may be slidably disposed on the distal end 210. The outer tube 204 and the inner tube 206 may extend through the connector piece 230. The outer tube 204 may be secured to the connector piece 230 so that it moves with the connector piece 230. The connector piece 230 may also be secured to the flexural element 228. Any suitable technique may be used for securing the connector piece 230 and the flexural element 228, such as first joint 234. The first joint 234 may include a first end connector 236 (e.g., a ball, a cylinder, etc.) at one end of the flexural element 228 moveably secured in a socket 238 on the connector piece 230. Any suitable technique may be used for securing the flexural element 228 to the cannula hub 107, such as a second joint 240. The second joint 240 may include a second end connector 242 (e.g., a ball, a cylinder, etc.) on the flexural element 228 moveably secured in a socket 244 on the cannula hub 107.

It should be understood that the actuator 202 shown in FIGS. 2 and 3 that includes the flexural element 228 and connector piece 230 is one example of a suitable actuator 202 that may be used for retraction of the cannula tip 110. Other suitable actuators may be used, including, but not limited to sliding sleeves, buttons, and the like that could cause relative movement of the outer tube 204 with respect to the cannula hub 107 and the inner tube 206.

Embodiments of the cannula assembly 108 may further include an outer tube 204 and an inner tube 206 disposed in the outer tube 204. As illustrated, the outer tube 204 and the inner tube 206 may be coaxially arranged. In some embodiments, the inner tube 206 may be slidably disposed in the outer tube 204, for example, so that the cannula tip 110 can be retracted into the outer tube 204. In some embodiments, the inner tube 206 may be secured to the cannula hub 107, and the outer tube 204 may be secured to the connector piece 230 so that movement of the connector piece 230 results in movement of the outer tube 204 with respect to the inner tube 206. Any suitable technique may be used for securing the outer tube 204 to the connector piece 230 and the inner tube 206 to the cannula hub 107, including, but not limited to, press fitting, adhesives, and/or fasteners.

The outer tube 204 may be formed from any suitable material. For example, suitable materials for the outer tube 204 may include, for example, a metal, such as stainless steel or titanium. However, the outer tube 204 may be formed from any suitable material, including, but not limited to, a polymer, metal, ceramic, or other suitable material. The outer tube 204 may have any suitable dimensions. For example, the outer tube 204 may have a length of about 20 millimeters to about 50 millimeters. By way of further example, the outer tube 204 may have an outer diameter of about 0.3 millimeters to about 1 millimeter. For example, the outer tube 204 may have a gauge size ranging from 20G to 27G, such as 20G, 23G, 25G, or 27G.

The inner tube 206 may be made from any suitable material. Suitable materials for the inner tube 206 may include, for example, a metal, such as stainless steel or titanium. However, the inner tube 206 may be formed from any suitable material, including, but not limited to, a polymer, metal, ceramic, or other suitable material. As previously described, the inner tube 206 may include a cannula tip 110 adapted to provide a cushioning and/or non-abrasive engagement with delicate tissues or membranes, such as in a patient's eye. In some instances, the cannula tip 110 adapted may be formed from any suitable soft material. Particularly, in some instances, the cannula tip 110 adapted may be formed from any medically compatible soft material. The cannula tip 110 adapted may be formed from materials including, for example, silicone, polyurethane, polyethylene, polypropylene, polystyrene, polytetrafluoroethylene, fluorinated ethylene propylene (FEP), perfluoroalkoxy (PFA), polyether ether ketone (PEEK), polyetherimide (PEI), polyamide imide (PAI), thermoplastic polyimides (TPI), polybenzimidazol (PBI), rubber, latex, combinations thereof, or other medically compat-ible polymers or plastic compounds. In some embodiments, the material forming the cannula tip 110 may have a durometer value of 80 A. In other instances, the material forming the cannula tip 110 may have a durometer value of about 50 A to 50 D. As used herein, durometer values are Shore hardness values as measured using ASTM D2250 type A and type D scales. However, this disclosure is not so limiting. Rather, these hardness values are provided merely as examples. Thus, the material forming the cannula tip 110 may have any desired hardness. In some embodiments, only the cannula tip 110 may be formed from these soft materials while the reminder of the inner tube 206 may made from a different material with a greater hardness, such as a polymer, metal, ceramic, or other suitable material.

The inner tube 206 may have any suitable dimensions. For example, the inner tube 206 may have a length of about 20 millimeters to about 55 millimeters. By way of further example, the inner tube may have an outer diameter of about 0.25 millimeters to about 0.49 millimeters. The cannula tip 110 may also have any suitable dimensions. For example, the cannula tip 110 may have a length of about 0.5 millimeters to about 10 millimeters. By way of further example, the cannula tip 110 may have an outer diameter of about 0.3 millimeters to about 0.4 millimeters.

An example embodiment for operation of the cannula assembly 108 for retraction of the cannula tip 110 will now be described with respect to FIGS. 2 and 3. In operation, the cannula assembly 108 may initially be in an extended (or initial) state with the cannula tip 110 extending beyond the outer tube 204 as shown on FIG. 2. For retraction, an operator may use the actuator 202 to cause the outer tube 204 to extend over the cannula tip 110, as shown on FIG. 3. For example, an actuator 202 may depress the flexural element 228 of the actuator 202 by application of radial force. As one end (shown as first end connector 236) of the actuator 202 is coupled to the connector piece 230, which is slidably disposed on the cannula hub 107, the connector piece 230 should slide longitudinally, as the flexural element 228 deforms, causing the flexural element 228 to lengthen. Since the connector piece 230 is coupled to the outer tube 204, the outer tube 204 is also moved longitudinally as the connector piece 230 is moved. The flexural element 228 may be depressed to cause sufficient movement of the outer tube 204 to cover the cannula tip 110, as shown on FIG. 3. As previously described, one or more stops 224 may be positioned on the cannula hub 107 to limit inward movement of the flexural element 228. When depressed, the flexural element 228 should store spring energy so that when released, the flexural element 228 should return to its original position, cause movement of the outer tube 204 in the longitudinal direction so that cannula tip 110 will again be extending from the outer tube 204, as shown on FIG. 3.

Figure 4:
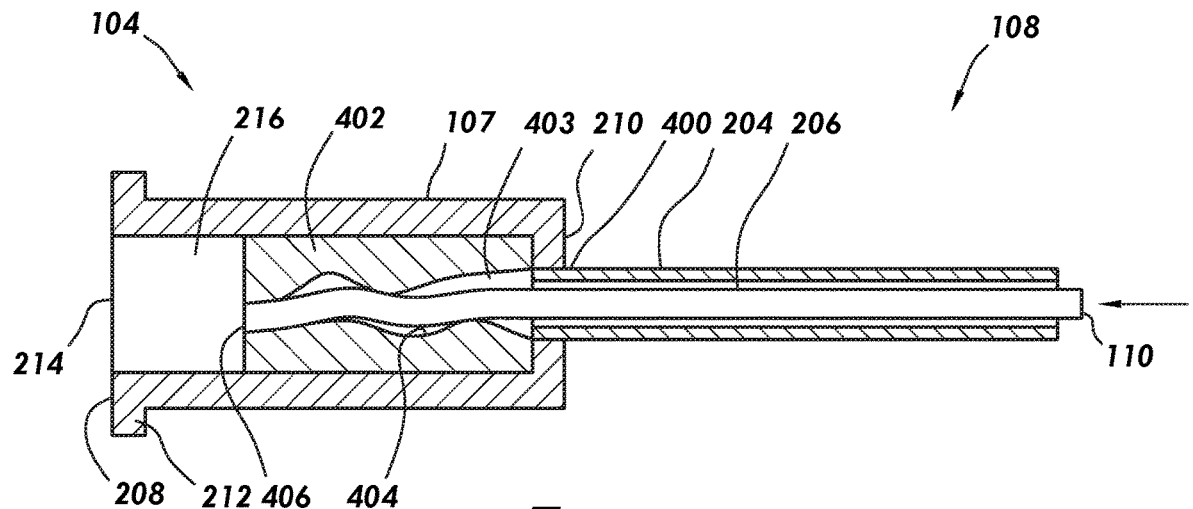
FIG. 4 is a cross-sectional side view of another example surgical instrument with a cannula tip in an extended position according to particular embodiments of the present disclosure.
Figure 5:
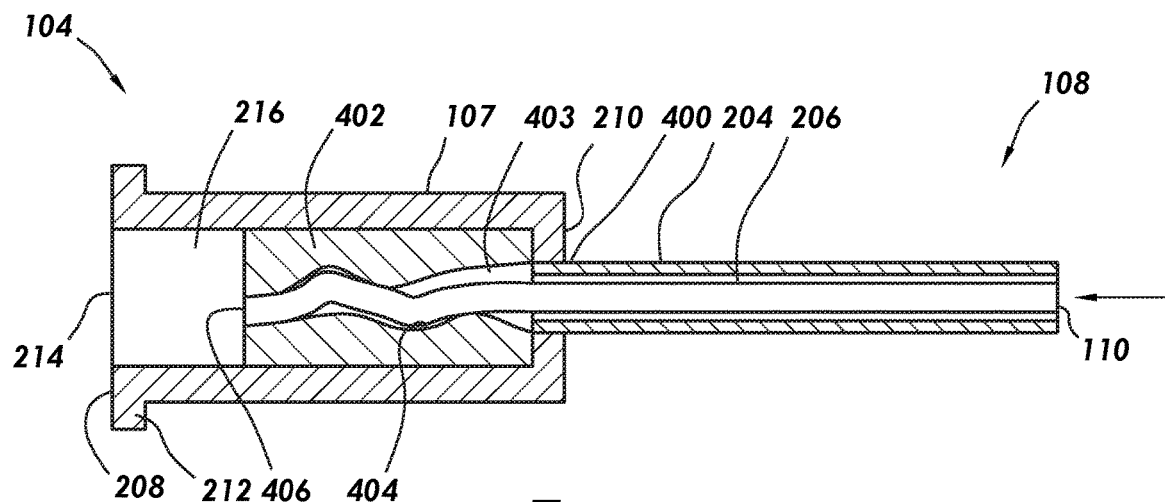
FIG. 5 is a cross-sectional side view of the example surgical instrument of FIG. 4 in a retracted position according to particular embodiments of the present disclosure.

FIGS. 4 and 5 illustrate another example embodiment of the cannula assembly 108. FIG. 4 illustrates the cannula tip 110 in an initial (or extended) position. FIG. 5 illustrates the cannula assembly 108 in a retracted position with the cannula tip 110 being fully retracted into the outer tube 204. As illustrated, the cannula assembly 108 may include a cannula hub 107, an outer tube 204, and an inner tube 206. The cannula assembly 108 may be used with any suitable instrument. In some embodiments, the cannula assembly 108 may be attached to the cannula hub 107 (e.g., shown on FIG. 1), which may be syringe, aspiration handle, or other suitable instrument. In other embodiments, the cannula assembly 108 may be attached directly to tubing (e.g., supply line 106 on FIG. 1).

The cannula hub 107 may include a proximal end 208 and a distal end 210. In the illustrated embodiment, the proximal end 208 includes a rim 212 and a proximal opening 214. The cannula hub 107 may define an inner chamber 216 opening into the proximal opening 214. While not shown, particular embodiments of the inner chamber 216 may receive a distal end of an instrument (e.g., cannula hub 107 on FIG. 1) or tubing (e.g., supply line 106 on FIG. 1) for mounting the cannula hub 107. The distal end 210 of the cannula hub 107 may include a distal opening 218. In the illustrated embodiment, the cannula hub 107 may further include a distal opening 218. As illustrated, inner tube 206 may extend through distal opening into the inner chamber 216. Outer tube 204 may be coupled to the cannula hub 107. For example, the outer tube 204 may be secured to the distal end 210 of the cannula hub 107. In some embodiments, the outer tube 204 may not extend into the cannula hub 107, but instead a proximal tube end 400 may be secured to the cannula hub 107.

The cannula hub 107 may further include a tube guidance 402. Tube guidance 402 may include any suitable device that can receive the inner tube 206 and include additional space 403 around the inner tube 206 to receive additional portions of inner tube 206 for retraction of the inner tube 206 into the outer tube 204. For example, the tube guidance 402 may be positioned in the inner chamber 216 of the cannula hub 107. In some embodiments, the tube guidance 402 may be a separate piece, but it is contemplated that the tube guidance 402 may also be unitary with the cannula hub 107. For example, the tube guidance 402 may include a channel 404 that receives a portion of the inner tube 206. In some embodiments, the inner tube 206 may be attached to the tube guidance 402, for example, at a proximal channel end 406. As illustrated, the channel 404 may have an undulating profile, which may be regular or irregular. The channel 404 may include the additional space 403 around the inner tube 206 that can receive additional portions of the inner tube 206 for retraction into the outer tube 204. For example, when force F is applied to the cannula tip 110, the inner tube 206 may be bend, buckle, or otherwise deform into the additional space 403 in the channel 404. The force F may be applied, for example, by an access cannula (e.g., working cannula 600 on FIG. 6). By moving into the additional space 403, the cannula tip 110 may be enabled to move proximally such that the cannula tip 110 may retract into the outer tube 204, as shown on FIG. 5. The inner tube 206 may store spring energy so that when the force F is removed, in some embodiments, the inner tube 206 may return to its initial position with cannula tip 110 extending beyond the outer tube 204. In addition to facilitating passage through an access cannula, this retraction may also protect portions of the eye (e.g., the retina) that may be inadvertently touched by the cannula tip 110 during surgery, as they the cannula tip 110 can retract as a result.

Figure 6:
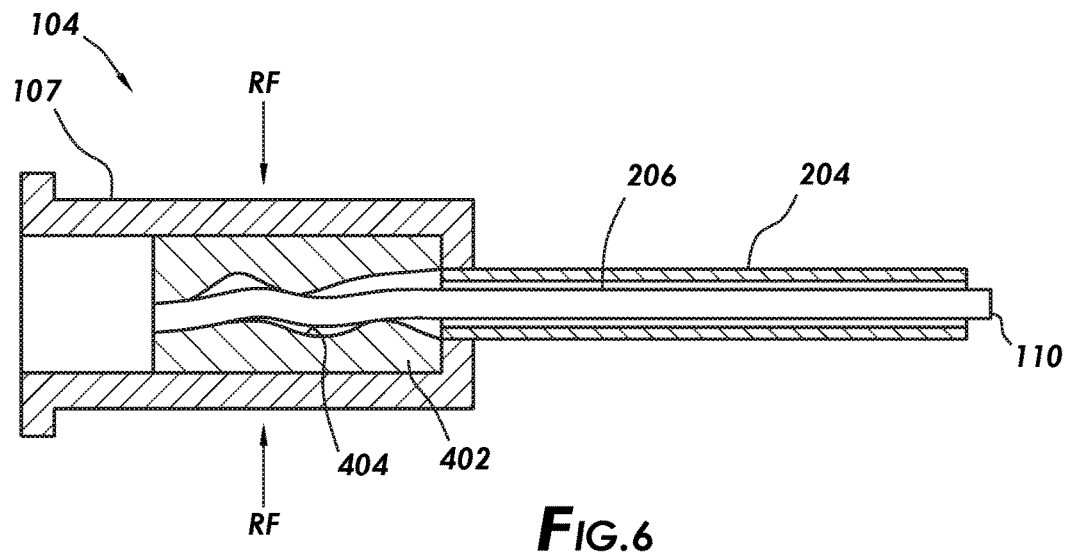
FIG. 6 is a cross-sectional side view of the example surgical instrument of FIG. 4 with a flexible cannula hub according to particular embodiments of the present disclosure.

FIG. 6 is an illustration of the example surgical instrument of FIG. 4 with the cannula hub 107 being flexible according to embodiments of the present disclosure. In the illustrated embodiment, the cannula hub 107 may be operable to actuate retraction of the cannula tip 110 into the outer tube 204. For example, the cannula hub 107 may be flexible so that upon application of radial force RF, the cannula hub 107 should flex inwards. By way of further example, the tube guidance 402 may also be flexible so that the tube guidance 402 should also flex inwards due to transfer of the radial force RF through the cannula hub 107. Flexing inward of the tube guidance 402 should constrict the channel 404 that contains the inner tube 206. However, particular embodiments may only constrict the channel 404 to a pre-defined position without undesirably compressing the inner tube 206. Any suitable technique may be used to limit constriction of the channel 404 include design of the undulating profile. Suitable flexible materials for the cannula hub 107 and/or the tube guidance 402 may include, but are not limited to, plastics and metals. An example of a suitable material for the cannula hub 107 and/or the tube guidance 402 may include a polycarbonate. Upon constriction of the channel 404, in some embodiments, the inner tube 206 may conform with the profile of the channel 404 causing deformation of the inner tube 206 with withdrawal of a portion of the inner tube into the cannula hub 107 such that the cannula tip 110 retracts into the outer tube 204. Upon release of the cannula hub 107, the cannula hub 107 and tube guidance 402 should return to their initial, uncompressed state such that the inner tube 206 extends longitudinally with the cannula tip 110 extending from the outer tube 204.

Figure 7:
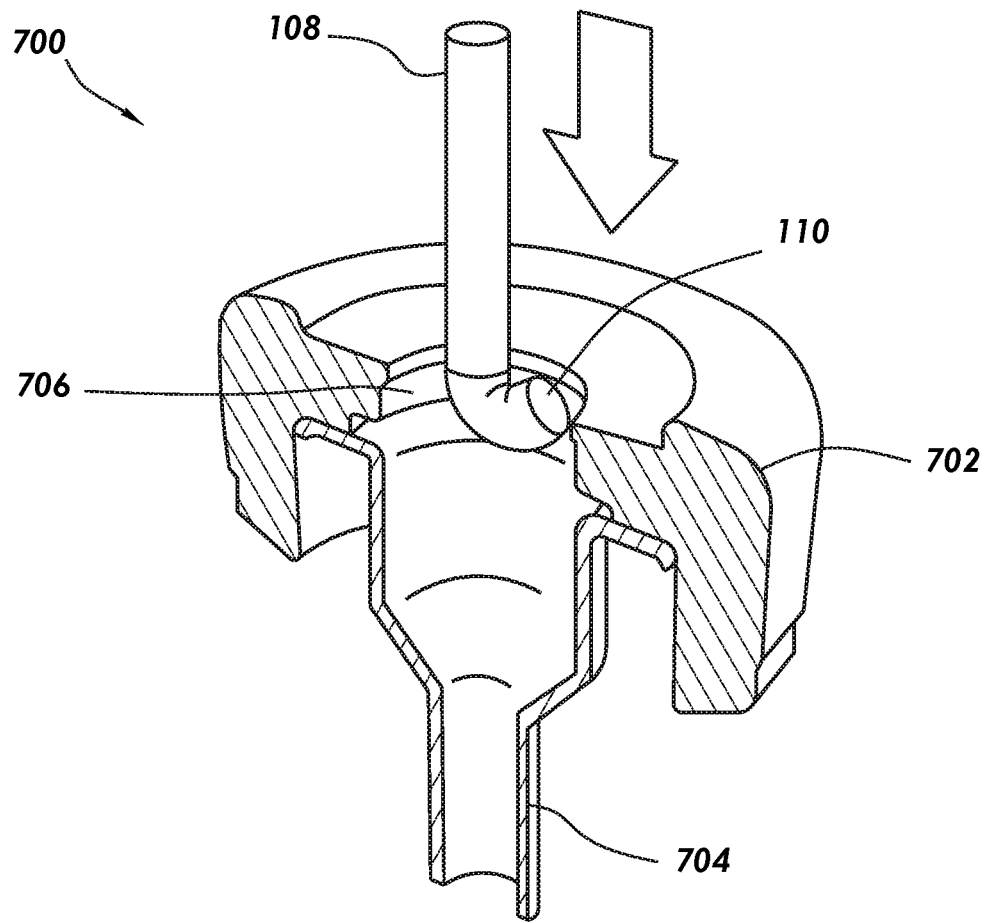
FIG. 7 is a partial cross-sectional view showing an example cannula assembly being inserted through an access cannula.

FIG. 7 illustrates an example of a working cannula 700 in accordance with particular embodiments of the present disclosure. In the illustrated embodiment, the working cannula 700 includes a hub 702 connected to a hollow tube 704. Embodiments of the hub 702 of the working cannula 700 may include a valve 706, which may be in the form of a slitted silicone diaphragm. In operation, a cannula assembly 108 may be inserted through the valve 706. However, if the cannula tip 110 is not retracted prior to insertion, the cannula tip 110 may undesirably bend rather than passing through the valve 706. Accordingly, particular embodiments of the present disclosure disclose retraction of the cannula tip 110 to facilitate insertion through the working cannula 700.

Figure 8:
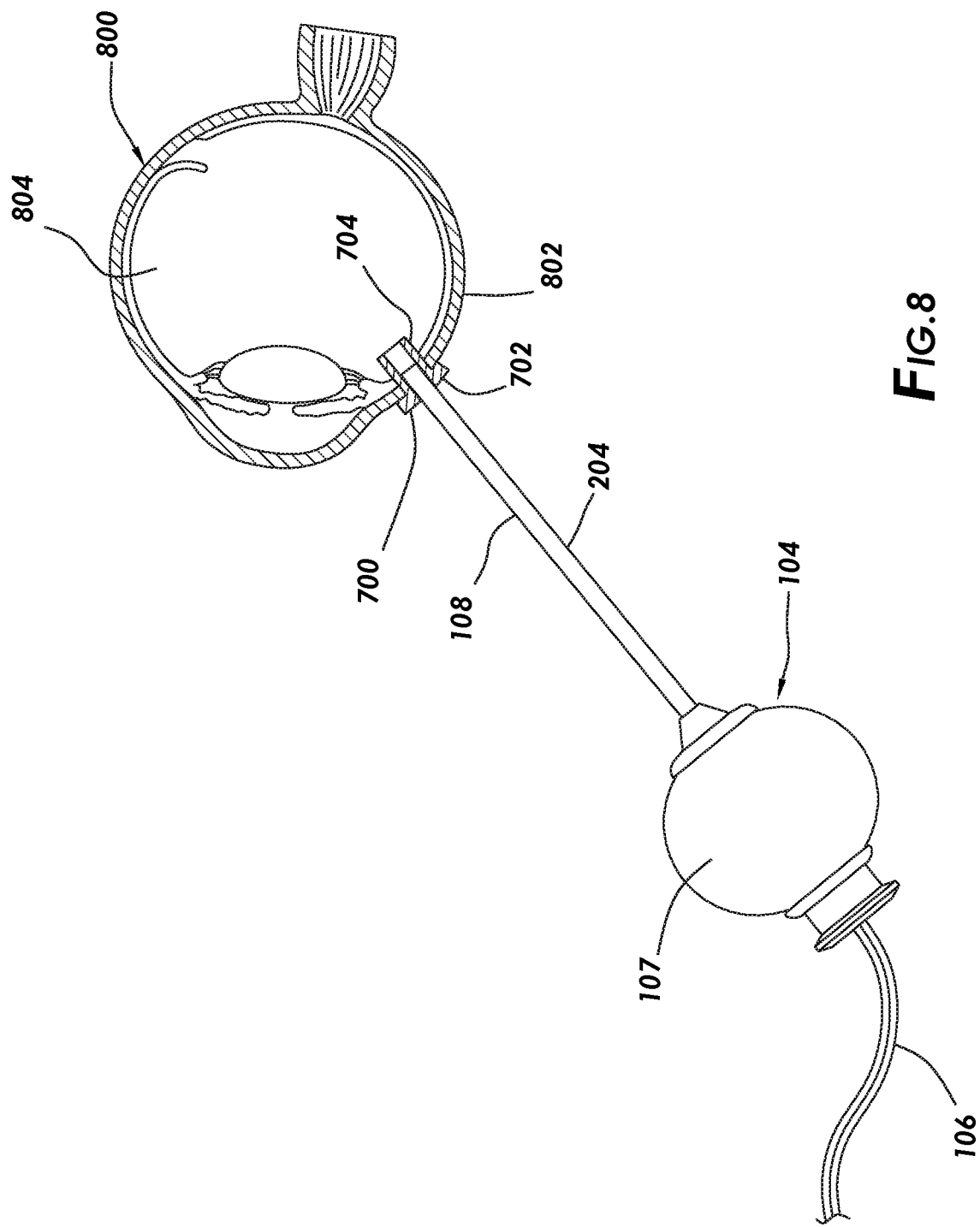
FIG. 8 is a partial cross-sectional view showing an example cannula assembly being inserted through an access cannula with the cannula tip in a retracted position according to particular embodiments of the present disclosure.
Figure 9:
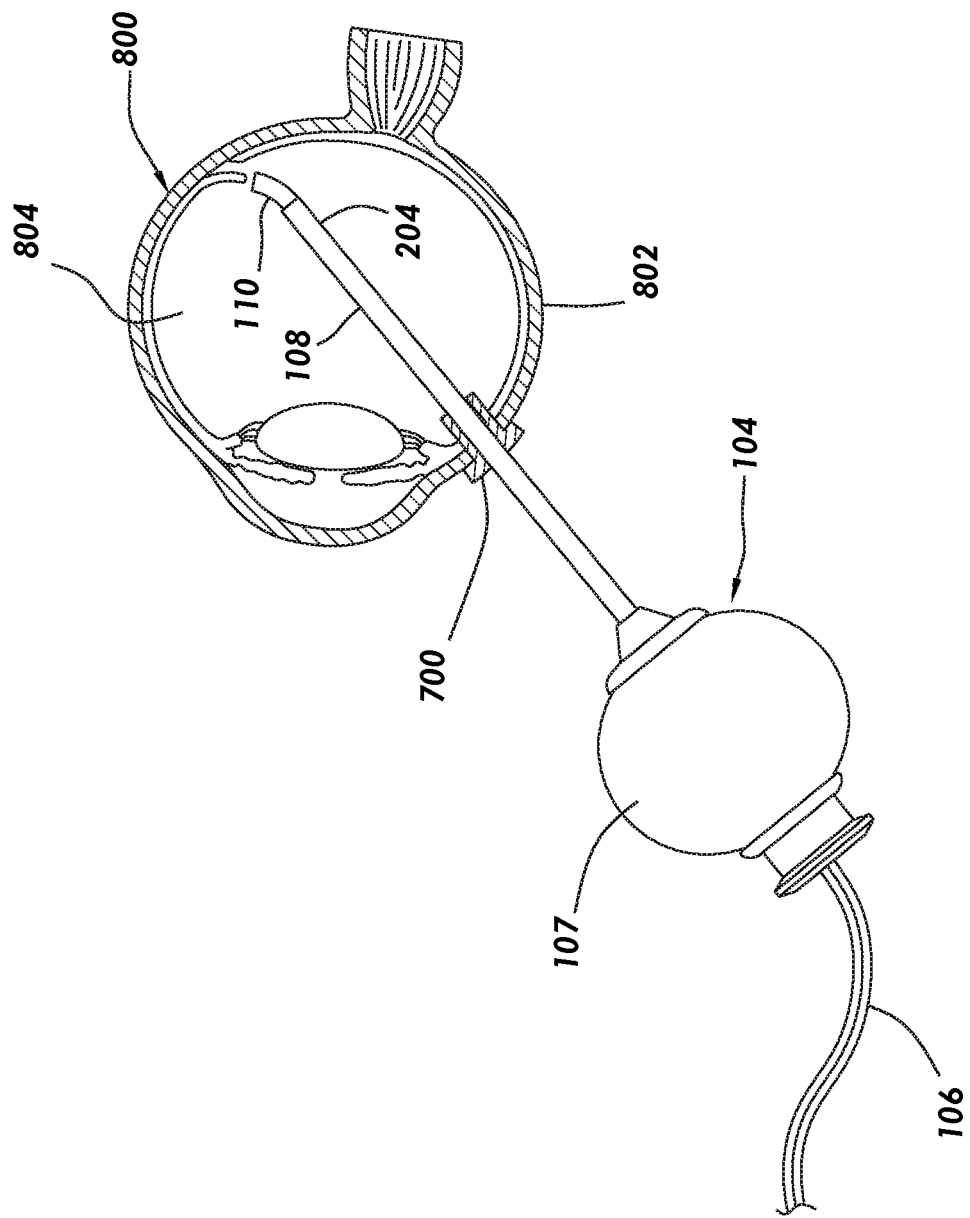
FIG. 9 is a partial cross-sectional view showing the example cannula shown in FIG. 7 advanced toward the retina of an eye with the cannula tip in an extended state according to particular embodiments of the present disclosure.

FIGS. 8 and 9 illustrate partial cross-sectional views of an eye 800 undergoing a procedure, which may involve the surgical instrument 104 according to an example method of the present disclosure. The surgical instrument 104 may be coupled to a console 102 (e.g., shown on FIG. 1) by way of the supply line 106. As illustrated, the surgical instrument 104 may include cannula hub 107 and cannula assembly 108. During the surgical procedure, the surgeon may insert a working cannula 700 into the eye 800 via an incision through the sclera 802. In FIG. 9, the surgical instrument 104 may be inserted through the working cannula 700 and into a vitreous chamber 804 of the eye 800. As illustrated, the cannula tip 110 may be retracted into the outer tube 204 (e.g., the outer tube 204 may be extended over the cannula tip 110 the cannula tip 110 may be withdrawn into the outer tube 204) of the cannula assembly 108 so that the cannula tip 110 is obstructed from view on FIG. 8. Because the cannula tip 110 is retracted, particular embodiments may facilitate insertion of the cannula assembly 108 through the hub 702 and into the hollow tube 704 without having to apply undue pressure on the cannula tip 110. FIG. 9 illustrates the cannula tip 110 extended from the outer tube 204 of the cannula assembly 108 after insertion through the working cannula 700 and into the eye 800.

It is believed that the operation and construction of the present disclosure will be apparent from the foregoing description. While the apparatus and methods shown or described above have been characterized as being preferred, various changes and modifications may be made therein without departing from the spirit and scope of the disclosure as defined in the following claims.

What is claimed is:

1. An apparatus for use in a surgical procedure, comprising:
   a cannula assembly comprising:
      a cannula hub;
      a connector piece configured to receive a distal end of the cannula hub;
      an outer tube that extends from the distal end of the cannula hub and is coupled to the connector piece;
      an inner tube that extends from the distal end of the cannula hub and is disposed in the outer tube; and
      an actuator comprising a first end connector coupled to the connector piece and a second end connector coupled to the cannula hub,
      wherein the actuator is configured to transition from an initial state into a deformed state when a force is applied to the actuator, and
      wherein the inner tube has a cannula tip that extends from the outer tube when the actuator is in the initial state and retracts into the outer tube as the actuator transitions from the deformed state into the initial state by a biasing force provided by the actuator.

2. The apparatus of claim 1, wherein the actuator comprises a first flexural element coupled at one end to the cannula hub and at another end to the outer tube, the outer tube being slidably disposed on the inner tube.

3. The apparatus of claim 2, wherein the connector piece is slidably disposed on the distal end of the cannula hub.

4. The apparatus of claim 3, wherein the first end connector and the second end connector each individually comprise an end connector of the first flexural element moveably coupled in a socket of the connector piece.

5. The apparatus of claim 2, further comprising a second flexural element, wherein the first flexural element and the second flexural element are disposed on opposing sides of the cannula hub.

6. The apparatus of claim 2, wherein the cannula hub comprises a stop extending from an outer surface of the cannula hub that limits inward flexing of the first flexural element.

7. The apparatus of claim 2, wherein the cannula hub defines an inner chamber opening into a proximal opening at a proximal end of the cannula hub, wherein the cannula hub further defines a lumen that extends from the inner chamber to the distal end of the cannula hub, wherein a portion of the inner tube extends into the lumen, the inner tube being secured to the cannula hub such that the outer tube can translate longitudinally with respect to the inner tube.

8. The apparatus of claim 1, wherein the cannula hub defines an inner chamber, wherein the outer tube is secured to the cannula hub and the inner tube extends through a distal opening in the inner chamber and into a tube guidance positioned in the inner chamber.

9. The apparatus of claim 8, wherein the tube guidance comprises a channel that receives the inner tube, wherein the channel has an undulating profile with additional space around the inner tube to receive additional portions of the inner tube.

10. The apparatus of claim 8, wherein a portion of the inner tube extending into the tube guidance is curved.

11. The apparatus of claim 1, wherein the cannula tip is a soft tip having a durometer value of about 50 A to about 50 D.

12. The apparatus of claim 1, wherein the cannula tip is formed from a material comprising silicone.

13. A system for ophthalmic surgical procedures, comprising:
a console comprising a housing, a display screen supported by the console, and a processor;
a cannula assembly comprising:
a cannula hub;
a connector piece configured to receive a distal end of the cannula hub;
an outer tube that extends from the distal end of the cannula hub and is coupled to the connector piece;
an actuator comprising a first end connector coupled to the connector piece and a second end connector coupled to the cannula hub;
an inner tube that extends from the distal end of the cannula hub and is disposed in the outer tube, wherein the inner tube has a cannula tip that extends from the outer tube when the actuator is in an initial state and retracts into the outer tube as the actuator transitions from a deformed state into the initial state by a biasing force provided by the actuator; and
a supply line configured to couple the cannula assembly to the console.

14. The system of claim 13, wherein the actuator further comprises a first flexural element coupled at one end to the cannula hub and at another end to a connector piece slidably disposed on the distal end of the cannula hub and secured to the outer tube.

15. The system of claim 14, wherein the connector piece is slidably disposed on the distal end of the cannula hub.

16. The system of claim 15, wherein the first end connector and the second end connector each individually comprise an end connector of the first flexural element moveably coupled in a socket of the connector piece.

17. The system of claim 14, further comprising a second flexural element, wherein the first flexural element and the second flexural element are disposed on opposing sides of the cannula hub.

18. The system of claim 14, wherein the cannula hub comprises a stop extending from an outer surface of the cannula hub that limits inward flexing of the first flexural element.

19. The system of claim 13, wherein the cannula hub defines an inner chamber, wherein the outer tube is secured to the cannula hub and the inner tube extends through a distal opening in the inner chamber and into a channel having an undulating profile and formed in a tube guidance positioned in the inner chamber.

20. The system of claim 13, wherein the cannula hub defines an inner chamber opening into a proximal opening at a proximal end of the cannula hub, wherein the cannula hub further defines a lumen that extends from the inner chamber to the distal end of the cannula hub, wherein a portion of the inner tube extends into the lumen, the inner tube being secured to the cannula hub such that the outer tube can translate longitudinally with respect to the inner tube.

* * * * *